United States Patent [19]

Burney et al.

[11] Patent Number: 4,986,814
[45] Date of Patent: Jan. 22, 1991

[54] ONE-PUNCH CATHETER

[75] Inventors: Bryan T. Burney; Steven L. Griffith; Francis J. Fry, all of Indianapolis, Ind.; Yue-Teh Jang, Houston, Tex.; Pamela M. Thornton; Vern L. Liebmann, both of Angleton, Tex.

[73] Assignee: Indianapolis Center for Advanced Research, Indianapolis, Ind.

[21] Appl. No.: 206,214

[22] Filed: Jun. 13, 1988

[51] Int. Cl.⁵ .......................................... A61M 5/178
[52] U.S. Cl. .................................. 604/164; 604/281; 604/166; 604/264
[58] Field of Search ............................. 604/164–166, 604/264, 280, 281, 29, 272, 51, 53, 167–170

[56] References Cited

U.S. PATENT DOCUMENTS

| | | |
|---|---|---|
| 3,312,220 | 4/1967 | Eisenberg ............................ 604/164 |
| 3,352,306 | 11/1967 | Hirsch ................................. 604/164 |
| 3,419,010 | 12/1968 | Williamson . |
| 3,459,189 | 8/1969 | Alley et al. . |
| 3,833,003 | 9/1974 | Taricco ............................... 604/164 |
| 3,860,006 | 1/1975 | Patel . |
| 3,946,741 | 3/1976 | Adair . |
| 3,993,079 | 11/1976 | Henriques de Gatztanondo . |
| 4,230,123 | 10/1980 | Hawkins, Jr. ......................... 604/51 |
| 4,351,333 | 9/1982 | Lazarus et al. ...................... 604/164 |
| 4,404,159 | 9/1983 | McFarlane . |
| 4,581,019 | 4/1986 | Curelaro et al. ..................... 604/164 |
| 4,588,398 | 5/1986 | Daugherty et al. . |
| 4,610,657 | 9/1986 | Densow . |
| 4,629,450 | 12/1986 | Suzuki et al. ....................... 604/164 |
| 4,668,221 | 5/1987 | Luther ................................ 604/168 |
| 4,671,795 | 6/1987 | Mulchin ............................. 604/264 |
| 4,699,611 | 10/1987 | Bowden ............................... 604/51 |
| 4,769,005 | 9/1988 | Ginsburg et al. .................... 604/164 |
| 4,772,264 | 9/1988 | Cragg ................................ 604/158 |

FOREIGN PATENT DOCUMENTS

| | | |
|---|---|---|
| 0245211A1 | 9/1987 | European Pat. Off. . |
| 3248067 | 7/1982 | Fed. Rep. of Germany . |
| 2481931 | 1/1979 | France . |
| WO83/00429 | 6/1983 | PCT Int'l Appl. . |

Primary Examiner—C. Fred Rosenbaum
Assistant Examiner—Kathleen A. Daley
Attorney, Agent, or Firm—Barnes & Thornburg

[57] ABSTRACT

A catheter assembly comprises a stylus including a first generally conically shaped end tapering to a point at a predetermined angle and a second end. A cannula includes a first lumen for slidably receiving the stylus. The cannula includes a first end having an end wall and a second end. A catheter includes a second lumen for slidably receiving the cannula, a first end and a second end. The first end of the catheter includes an end wall having an outer surface tapered at the predetermined angle and an inner surface. The stylus, cannula, and catheter are configured so that the stylus, cannula, and catheter are aligned when the stylus, cannula and catheter are assembled for insertion into a patient's body. The first end of the stylus projects from the first end of the cannula, the tapered outer surface of the end wall of the catheter is aligned to be substantially coincident with the generally conically shaped end of the stylus to form a generally conical tip portion of the catheter assembly, and the end wall of the cannula abuts the inner surface of the end wall of the catheter to facilitate insertion of the catheter assembly into the patient's body.

4 Claims, 2 Drawing Sheets

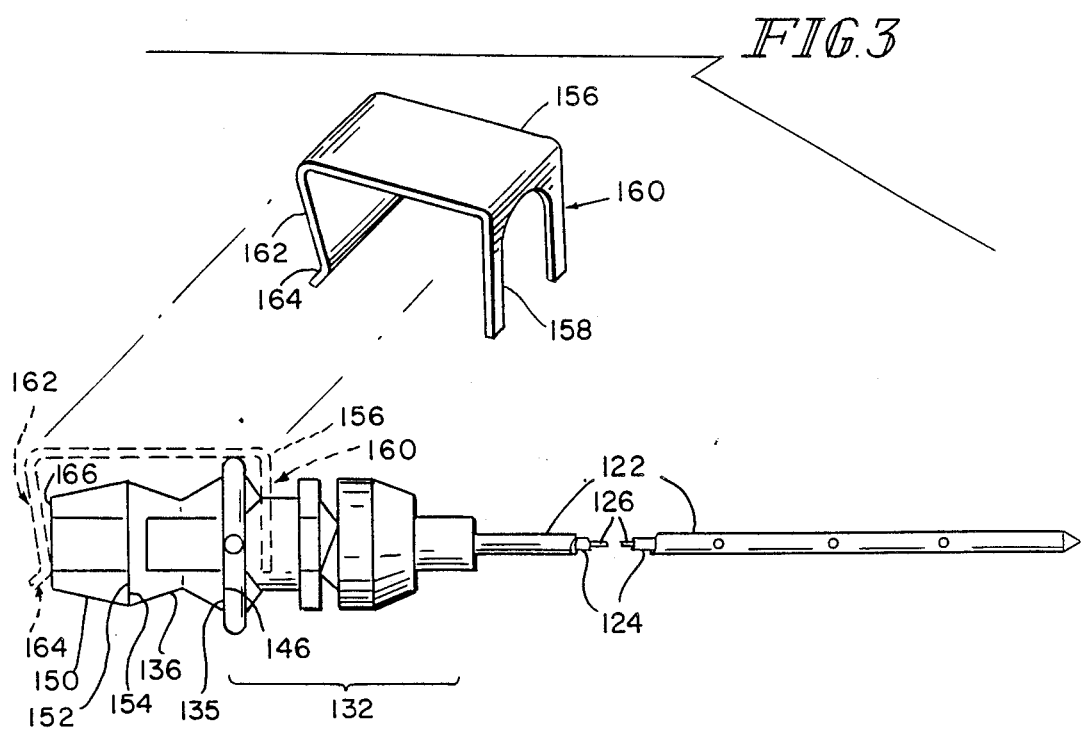

ONE-PUNCH CATHETER

This invention relates to medical instruments and particularly to a three-component catheter system. The system is useful, for example, in the introduction of chemical species into a region, such as an organ or a cavity, in the body of a patient for chemical treatment.

The introduction of chemical species into various body regions for diagnostic and treatment purposes is well known. An example of such a treatment is the use of various chemical species such as monooctanoin, methyl tert-butyl ether (MTBE), and other chemical species in the dissolution of cholesterol-based gallstones in the gall bladder and bile duct system. In some cases, the chemical species are introduced into the gall bladder and ducts through transesophageal catheter. In others, the method of introduction of choice is transcutaneous catheterization.

A problem with many transcutaneous catheter systems is that the ends of the system components are not appropriately shaped to puncture the skin and the intervening tissue between the skin and the treatment site. Some catheter systems have blunt, flat ends. Some catheter systems have some tapered components which would ease their penetration of tissue to the treatment site, but their designs make them difficult to use.

It is an object of the present invention to provide a catheter system the components of which can be locked together for one-step insertion, and which is tapered for easy tissue puncture, illustratively under ultrasound guidance.

According to one aspect of the invention, the catheter system includes a stylus and cannula for providing rigidity to the system during insertion of the catheter. The stylus has a first diamond-shaped tip end tapering to a point and a second end. The system further includes a cannula having an inside diameter for slidably receiving the stylus and an outside diameter, the cannula having a first end wall and a second end. The catheter system also includes a catheter having an inside diameter for slidably receiving the outside diameter of the cannula and first and second ends. The second ends of the stylus, cannula and catheter include relative placement means such that, when the stylus, cannula and catheter are assembled for insertion, the first end of the stylus projects from the first end of the cannula. The catheter first end includes a first end wall which is generally frustoconically shaped and substantially coincident with the conical shape of the first end of the stylus.

According to this aspect of the invention, the inside diameter of the catheter is defined by an inner sidewall. The catheter further includes an outer sidewall defining an outside diameter of the catheter. The catheter includes at least one port extending between its outer sidewall and its inner sidewall adjacent its first end. Illustratively, the catheter includes a plurality of ports spaced longitudinally from each other along the sidewall of the catheter. Further, illustratively, the ports are generally elliptical. The major axes of the ports extend generally longitudinally of the apparatus and the minor axes of the ports extend generally transversely of the apparatus around the catheter.

Additionally, according to this aspect of the invention, the catheter includes a portion preformed so that it tends to provide a loop, the loop-forming portion including the first end and an adjacent region of the catheter. The loop-forming portion aids in anchoring the catheter in a body region or organ into which the first end of the catheter is placed, and also aids in the insertion of the catheter into a generally round body cavity.

Illustratively, according to this aspect of the invention, the loop-forming portion of the catheter is formed from extruded nylon.

The invention may best be understood by referring to the following description and accompanying drawings which illustrate the invention. In the drawings.

Figure 1:
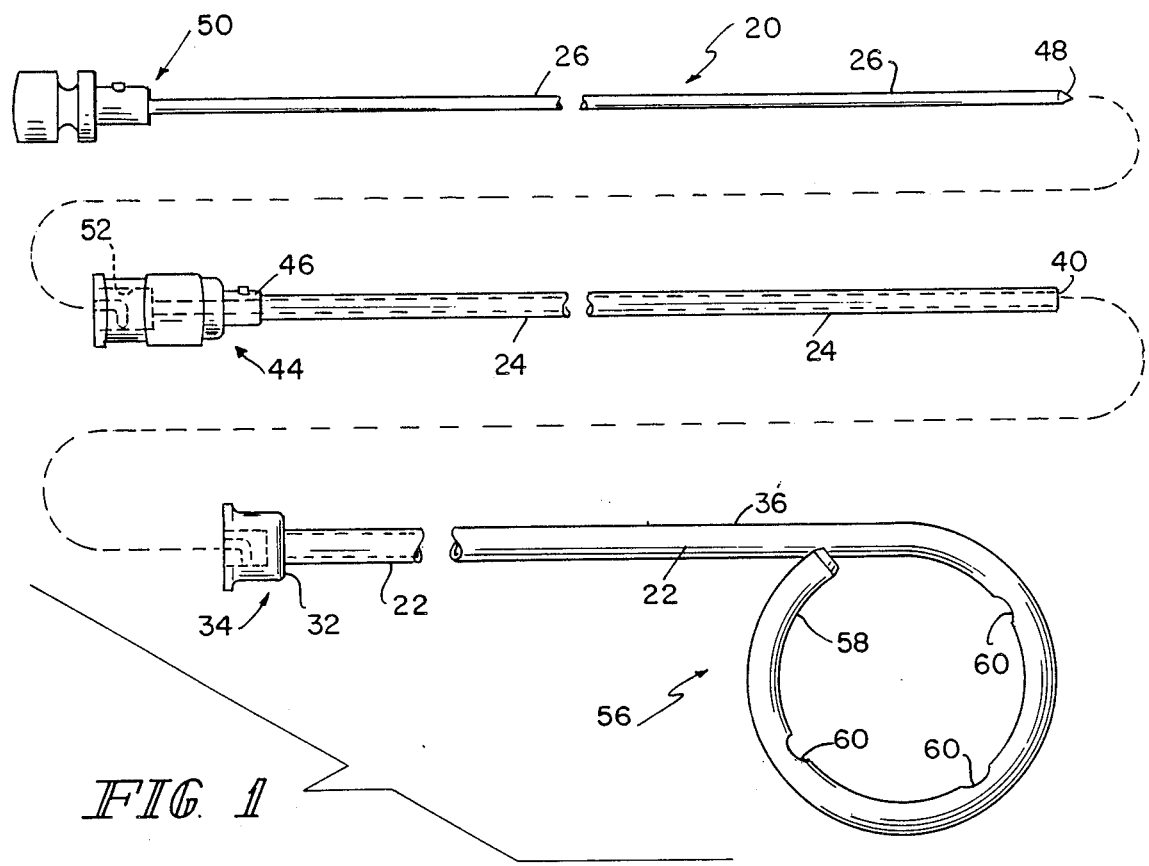
FIG. 1 illustrates an exploded side elevational view of the components of the catheter system of the present invention.
Figure 2:
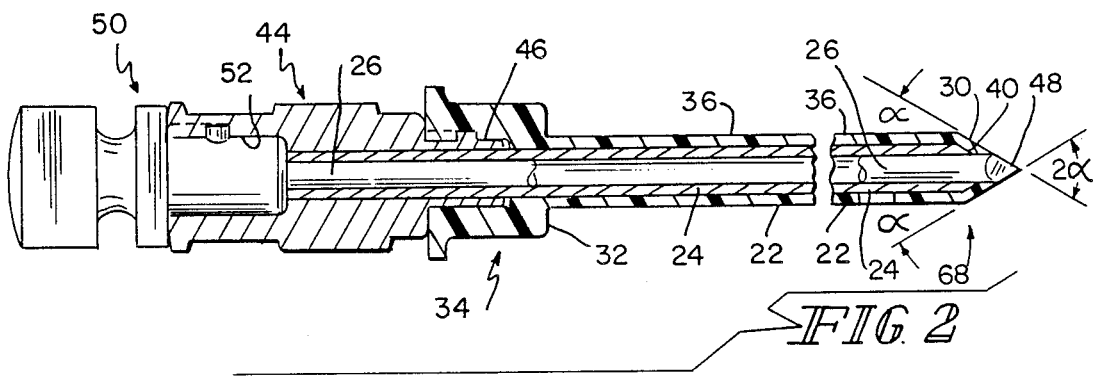
FIG. 2 illustrates an enlarged, fragmentary, longitudinal sectional side elevational view of the ends of the assembled components of FIG. 1.; and, FIG. 3 illustrates an enlarged, fragmentary, partly longitudinal sectional side elevational, and partly perspective, view of the ends of another embodiment of the assembled components.

Turning now to FIGS. 1-2, the catheter system 20 of the present invention includes the catheter 22 itself, a cannula 24, and a solid needle stylus 26. The catheter 22 itself is illustratively formed from 4 French biocompatible material, such as extruded nylon material.

Catheter 22 includes an end wall 30 of substantially the same thickness as the uniform thickness of its sidewall 36. However, end wall 30 tapers from the 4 French sidewall diameter to a diameter of 0.020 inch (5 mm). The angle of the taper is labelled $\alpha$ and is illustratively in the range of 15°–30°. The catheter 22 has a usable length of, for example, 25 cm. from its tapered end wall 30 to the base 32 of a locking member 34, such as the female part of a LEUR-LOK locking mechanism.

The cannula 24 has a bevelled end wall 40 formed to include an angle of approximately $\alpha$. A length of just slightly less than 25 cm. of cannula 24 protrudes beyond the base 32 of locking member 34 of catheter 22 when the cannula 24 is inserted into catheter 22 to the depth permitted by a locking member 44 fitted to the end of cannula 24 opposite its bevelled end wall 40. Locking member 44 illustratively has a male LEUR-LOK forward locking surface 46 which engages the female LEUR-LOK part 34 of catheter 22 when cannula 24 is inserted into catheter 22. Cannula 24 illustratively is constructed from 21 gauge thin-wall biocompatible stainless steel tubing.

The stylus 26 is a solid biocompatible stainless steel needle with a diamond-shaped tip 48 at one end and a locking member 50 at the other end. Locking member 50 illustratively is a male LEUR-LOK member for engagement with a female LEUR-LOK surface 52 provided on the locking member 44 of cannula 24. The diameter of stylus 26 is 0.020 inch (0.5 mm). The length of stylus 26 is such that, when locking members 50, 52 are engaged, tip 48 protrudes beyond the bevelled end wall 40 of cannula 24 approximately the wall thickness of end wall 30 of catheter 22 times the cosecant of the angle $\alpha$. The tip 48 of stylus 26 is also as nearly as possible symmetrical about the axis of the catheter system 20 and includes an angle as nearly as possible equal to $2\alpha$. This bevel or taper and end configuration effectively "matches" the end 48 of the stylus 26 to the end wall 30 of the catheter 22. This is done for ease of insertion of the catheter system 20 as will be explained more fully later.

As best illustrated in FIG. 1, when the stylus 26 and cannula 24 are removed from an end region 56 of the catheter 22, the end region 56 forms itself into a curl or so-called "pigtail" of illustratively circular configuration and about 2 cm. diameter. The effect is achieved, for example, by prestressing the end region 56 into this configuration during the process of forming catheter 22. The "memory" of the material, illustratively extruded nylon, from which catheter 22 is constructed causes region 56 to return to this configuration whenever it is not being held in some other configuration, such as by cannula 24. The inner curve 58 formed by the pigtail region 56 when cannula 24 is removed is provided with a plurality, illustratively three, of openings 60 through the catheter 22 sidewall 62. The openings 60 are longitudinally spaced at, for example, 0.5 cm.–1.5 cm. intervals with the closest of these openings 60 to the end wall 30 being 0.5 cm.–1.5 cm. from end wall 30. The openings 60 are illustratively elliptical with their minor axes extending generally perimetrally around the sidewall 36, of catheter 22 and their major axes extending generally longitudinally of catheter 22.

In use, let it be assumed that the catheter 22 is going to be used to drain a patient's gall bladder and/or to introduce irrigants into the patient's gall bladder. The system 20 comprising the catheter 22, cannula 24 and stylus 26 is assembled so that the tip 68 of the system is as illustrated in FIG. 2. The tip 68 is then poked through the skin of the patient's abdomen adjacent the gall bladder. The tip 68 is then poked through the peritoneum and finally through the wall of the gall bladder. It will be appreciated that the locking of the components 22, 24, 26 together during this portion of the procedure permits grasping the outside of the catheter 22 itself to help minimize the likelihood that force applied at a location remote from tip 68 will cause the catheter system 20 to flex instead of to penetrate the tissue. It will also be appreciated that the end configuration of the catheter system including the tapered end wall 30 of catheter 22 and the end wall 40 of cannula 24 aids in preventing end wall 30 from "bunching up" or sliding rearwardly toward the locking member 34 during this procedure. It is important to this operation that minimum clearance be provided between the outer sidewall of cannula 24 and the inner sidewall of catheter 22. Once the catheter tip region 56 has passed through the intervening tissue into the gall bladder, it is necessary to insure that the catheter is properly positioned in the gall bladder. For this purpose the stylus 26 can be removed from the cannula 24 and a guidewire (not shown) such as a 0.018 inch (0.46 mm) Lunderquist guidewire can be inserted into the catheter/cannula. The guidewire is threaded down the lumen of the cannula 24 and into the gall bladder. The guidewire will encounter resistance, indicating contact of the stiff part of the guidewire with the opposite interior wall of the gall bladder. The catheter is then released from the cannula and the catheter is advanced along the guidewire while the cannula is maintained stationary. This advancement is stopped when the pigtail is anchored entirely within the gall bladder. The guidewire and cannula are then removed. The openings 60 are exposed and open toward the interior, rather than the wall, of the gall bladder. This reduces the likelihood that the tissue of the wall of the gall bladder will restrict the flow of fluid through the openings 60. Suitable drainage and/or irrigation equipment can then be attached to locking member 34.

In another embodiment of the locking portions of a catheter 122, cannula 124 and stylus 126, illustrated in FIG. 3, the catheter 122 includes a base 132. The cannula 124 includes a base 136 having a surface 146 which is configured to abut a surface 135 of base 132 on catheter 122. Stylus 126 includes a base 150 having a surface 154 configured to abut a surface 152 provided on base 136. A locking clip 156, illustrated in perspective in solid lines and in place on the catheter assembly in broken lines, is somewhat U-shaped in elevation and has a somewhat U-shaped opening 158 formed in one, 160, of its generally parallel legs 160, 162. The other leg, 162 is formed with a slight bend 164 and clip 156 is constructed from a resilient material. When catheter 122, cannula 124 and stylus 126 are assembled for insertion, clip 156 can be snapped into its position in which leg 162 encompasses the outer end 166 of base 150 and opening 158 receives base 132. This effectively clamps the components 122, 124, 126 in their assembled orientation for insertion.

What is claimed is:

1. A catheter assembly comprising a stylus including a first generally conically shaped end tapering to a point at a predetermined angle and a second end,
   a cannula including a first lumen for slidably receiving the stylus, the cannula including a first end having an end wall and a second end,
   a catheter including a second lumen for slidably receiving the cannula, the catheter having a first end and a second end, the first end of the catheter including an end wall having an outer surface tapered at the predetermined angle and an innter surface, and
   means for aligning the second ends of the stylus, cannula, and catheter so that when the stylus, cannula, and catheter are assembled for insertion into a patient's body, the first end of the stylus projects from the first end of the cannula, the tapered outer surface of the end wall of the catheter is aligned to be substantially coincident with the generally conically shaped end of the stylus to form a generally conical tip portion of the catheter assembly, and the end wall of the cannula abuts the inner surface of the end wall of the catheter to facilitate insertion of the catheter assembly into the patient's body.

2. The assembly of claim 1, wherein the second lumen is defined by an inner sidewall, the catheter further including an outer sidewall and the catheter includes at least one port extending between its outer sidewall and its inner sidewall adjacent to its first end.

3. The assembly of claim 1, wherein the catheter includes a portion performed so that it tends to provide a loop when the cannula and stylus are removed from the catheter, the loop-forming portion including the first end and an adjacent region of the catheter.

4. The assembly of claim 1, wherein the inner surface of the end wall of the catheter is tapered and the end wall of the cannula is bevelled.

* * * * *